United States Patent
Keasling et al.

(10) Patent No.: US 10,167,488 B2
(45) Date of Patent: Jan. 1, 2019

(54) HETEROLOGOUS PATHWAY TO PRODUCE TERPENES

(71) Applicant: The Regents of the University of California, Oakland, CA (US)

(72) Inventors: Jay D. Keasling, Berkeley, CA (US); Christopher B. Eiben, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/803,735

(22) Filed: Nov. 3, 2017

(65) Prior Publication Data

US 2018/0119176 A1   May 3, 2018

Related U.S. Application Data

(60) Provisional application No. 62/417,299, filed on Nov. 3, 2016.

(51) Int. Cl.

| | |
|---|---|
| *C12P 5/00* | (2006.01) |
| *C12N 15/52* | (2006.01) |
| *C12N 9/10* | (2006.01) |
| *C12N 9/04* | (2006.01) |
| *C12N 9/88* | (2006.01) |
| *C12N 9/90* | (2006.01) |
| *C12N 9/12* | (2006.01) |
| *C12P 9/00* | (2006.01) |

(52) U.S. Cl.
CPC ............ *C12P 5/007* (2013.01); *C12N 9/0006* (2013.01); *C12N 9/1025* (2013.01); *C12N 9/1029* (2013.01); *C12N 9/1085* (2013.01); *C12N 9/1205* (2013.01); *C12N 9/88* (2013.01); *C12N 9/90* (2013.01); *C12N 15/52* (2013.01); *C12P 9/00* (2013.01); *C12Y 101/01034* (2013.01); *C12Y 203/01009* (2013.01); *C12Y 203/0301* (2013.01); *C12Y 205/01001* (2013.01); *C12Y 207/01036* (2013.01); *C12Y 402/03027* (2013.01); *C12Y 503/03002* (2013.01)

(58) Field of Classification Search
CPC . C12P 5/007; C12P 9/00; C12N 15/52; C12N 9/1025; C12N 9/0006; C12N 9/88; C12N 9/90; C12N 9/1085; C12N 9/1205; C12N 9/1029; C12Y 207/01036; C12Y 203/01009; C12Y 203/0301; C12Y 101/01034; C12Y 402/03027; C12Y 503/03002; C12Y 205/01001
See application file for complete search history.

(56) References Cited

PUBLICATIONS

Kinjoh et al., Insect Biochemistry and Molecular Biology 37:808-818, 2007.*
Witkowski et al., Biochemistry 38:11643-11650, 1999.*
Seffernick et al., J. Bacteriol. 183(8):2405-2410, 2001.*
Sen et al., Insect Biochemistry and Molecular Biology 37:819-828, 2007.*
Branden et al., Introduction to Protein Structure, Garland Publishing Inc., New York, p. 247, 1991.*
Sadowski et al., Current Opinion in Structural Biology 19:357-362, 2009.*
Cascón et al., Chem. Commun. 48:9702-9704, 2012.*

* cited by examiner

*Primary Examiner* — Delia M Ramirez
(74) *Attorney, Agent, or Firm* — Richard Aron Osman

(57) ABSTRACT

Cells comprising a heterologous metabolic pathway are configured to produce a terpene product containing non-multiples of five carbon, particularly wherein the pathway comprises heterologous Lepidoptera insect juvenile hormone biosynthetic pathway enzymes of the insect's mevalonate pathway.

7 Claims, 5 Drawing Sheets

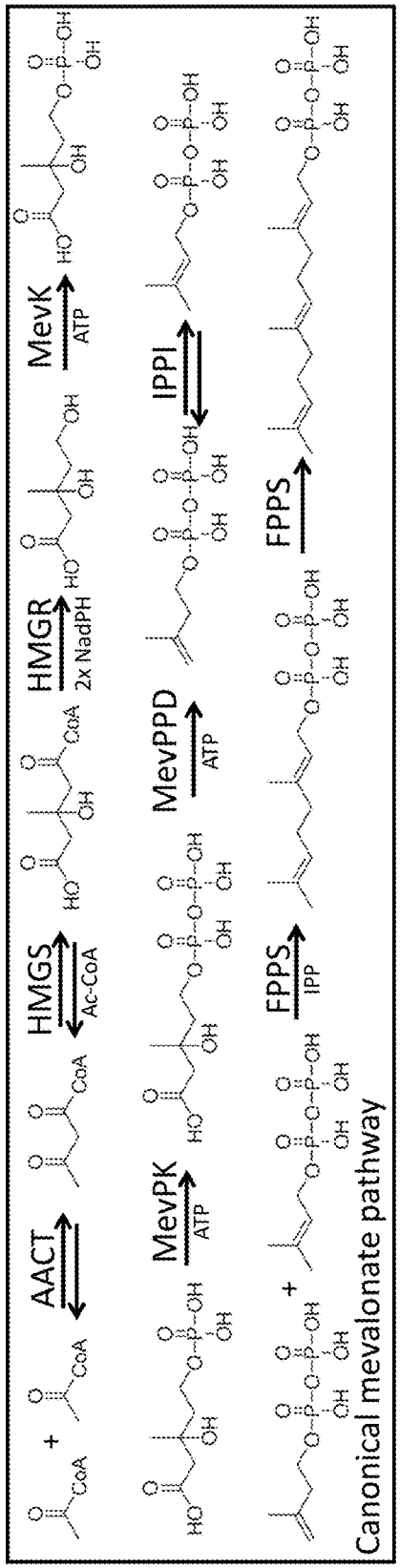
Fig. 1 Canonical mevalonate pathway
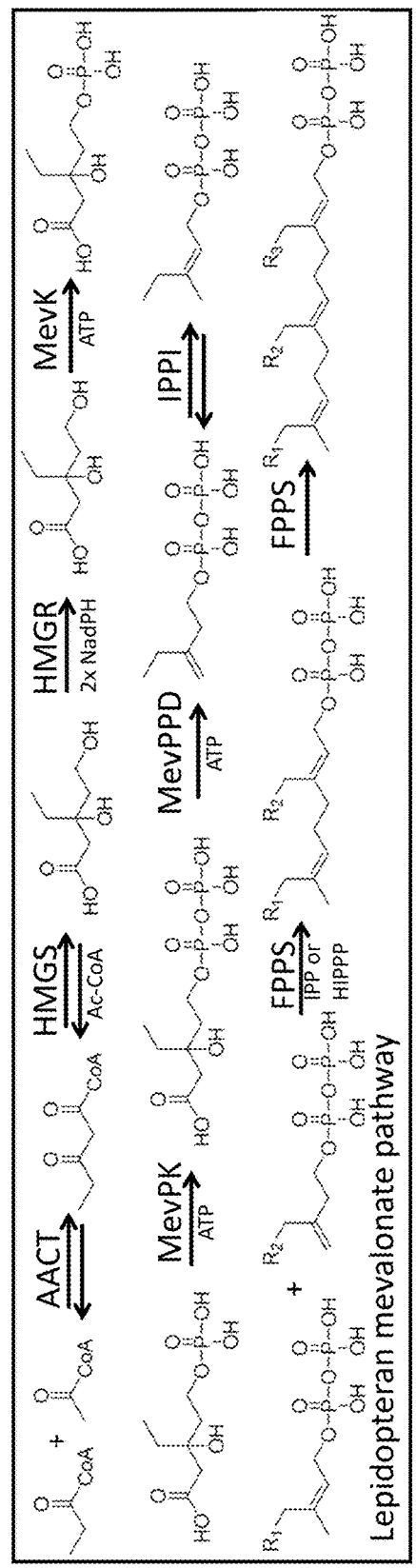
Fig. 2 Lepidopteran mevalonate pathway

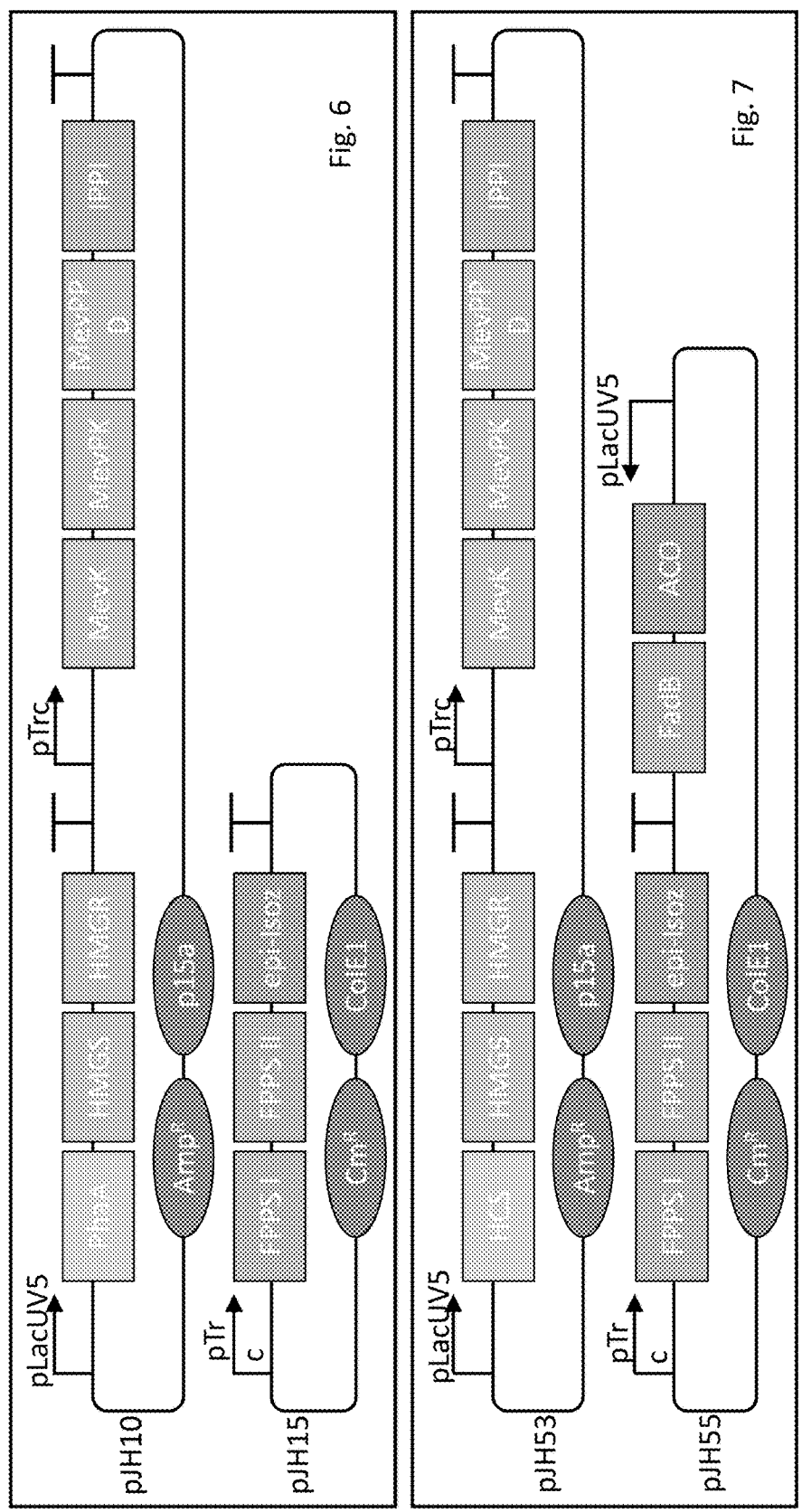

HETEROLOGOUS PATHWAY TO PRODUCE TERPENES

This invention was made with government support under Grant Number GM008295 awarded by the National Institutes of Health, Grant Numbers 1106400 and 0540879 awarded by the National Science Foundation and Contract Number DE-AC02-05CH11231 awarded by the Department of Energy. The government has certain rights in the invention."

INTRODUCTION

Terpenes are the largest class of natural products estimated to contain between 55,000 and 70,000 members. Because of the diversity in terpenes they find uses in a variety of industries as pharmaceuticals, flavors, fragrances, commodity chemicals and fuels. Despite their diversity, terpenes are derived from two interconvertible five carbon containing compounds, IPP and DMAPP. For this reason, the backbone of almost all terpenes start as multiples of five carbons during their biosynthesis. Lepidoptera and some closely related organisms possess the ability to produce the six carbon compounds HIPP and EMAPP, which they use to make juvenile hormones (JHs).

Relevant literature: Kinjoh et al., Insect Biochem Mol Biol. 2007 August; 37(8):808-18; Sen S E et al. Insect Biochem Mol Biol. 2012 October; 42(10):739-50; Sen S E et al. Insect Biochem Mol Biol. 2007 August; 37(8):819-28; Cusson M. et al. Proteins. 2006 Nov. 15; 65(3):742-58; Cascón O, Chem Commun (Camb). 2012 Oct. 9; 48(78): 9702-4.

SUMMARY OF THE INVENTION

The invention provides methods and compositions for producing a terpene product comprising a carbon number that is not a multiple of five (a non-multiple of five carbon), such as a multiple of six carbons. In one aspect the invention provides a cell comprising a heterologous metabolic pathway configured to produce a terpene product comprising a carbon number other than a multiple of five carbons.

In embodiments:
 the cell comprises the terpene metabolic product of the pathway.
 the pathway comprises heterologous insect juvenile hormone biosynthetic pathway enzymes, such as of the insect's mevalonate pathway, such as wherein the insect is a Lepidoptera or non-lepidoptera insects that can make homomevalonate based on natural products such as juvenile hormones, such as wherein the enzymes are selected from or include 1, 2, 3, 4, 5, 6, 7 or all 8 of: HMGS, HMGR, MevK, MevPK, MevPPD, IDI, and FPPS (one or both of FPPS I and FPPS II).
 the pathway comprises a terpene cyclase.
 the terpene product is a C11, C12, C16, C17, C18 or C21-24 terpene.
 the terpene product comprises an ethyl substitution of a methyl group.

The invention provides and enables production of a variety of compounds, such as wherein the terpene product is selected from homomevalonate for polymers or specialty chemicals, homoisoprene for polymers and specialty chemicals, C11 and C12 "monoterpenes" for all terpene applications, including pharmaceuticals, flavors, fragrances, commodity chemicals and fuels, C16, C17, C18 "sesquiterpenes" for all terpene applications, including pharmaceuticals, flavors, fragrances, commodity chemicals and fuels, higher terpenes (diterpenes, squalene, etc).

In embodiments:
 the pathway includes a 3-ketovaleryl-CoA intermediate and comprises a thiolase to condense propionyl-CoA and acetyl-CoA together, an enzyme which catalyzes a decarboxylative claisen condensation of propionyl-CoA and malonyl-CoA, or beta oxidation on valerate or other odd chain fatty acid.
 the pathway comprises expressing lepidopteran (or functionally equivalent) HMGS and HMGR (truncated) heterologously along with the first three steps of the beta-oxidation pathway, to make homomevalonate from valerate.
 the pathway comprises expressing lepidopteran HMGS and HMGR (truncated), MevK, MevPK and MevPPD heterologously and an isoprene synthase along with the first three steps of the beta-oxidation pathway, to make homoisoprene from valerate.
 the pathway comprises expressing lepidopteran HMGS and HMGR, MevK, MevPK, MevPPD, IDI, and FPPS heterologously with a terpene cyclase along with the first three steps of the beta-oxidation pathway, to make C11 and C12 monoterpenes from valerate; in another embodiment, the intermediates of the beta oxidation pathway (with a suitable CoA ligase) can be fed to the cells to make 3-ketovaleryl-CoA from which homomevalonate and homoterpenes can be made.
 the pathway comprises expressing lepidopteran HMGS and HMGR, MevK, MevPK, MevPPD, IDI, and FPPS heterologously along with the first three steps of the beta-oxidation pathway, to make C16, C17, C18 sesquiterpenes from valerate.

In another aspect the invention provides methods of producing a terpene product containing non-multiples of five carbon comprising growing a subject cell to produce the product, and optionally isolating, concentrating or enriching the product.

In another aspect the invention provides methods of making a subject cell comprising genetically engineering the cell or a precursor of the cell to comprise the pathway.

The invention encompasses all combination of the particular embodiments recited herein, as if each combination had been laboriously recited.

BRIEF DESCRIPTION OF THE FIGURES

FIG. 1. Canonical mevalonate pathway
FIG. 2. Lepidopteran mevalonate pathway
FIG. 3. GC Single Ion Chromatogram 218 Corresponding to C16 Terpene; inset: Enriched Sample Shows C16 Terpene Consistent Fragmentation Pattern
FIG. 4. Several Juvenile hormones found in nature, and intermediates
FIG. 5. Alternative Starting Units
FIGS. 6, 7. Pathway Expression Vectors
FIG. 8. Alternative R groups

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Canonical Mevalonate Pathway:

The canonical mevalonate pathway starts with the condensation of two acetyl-CoAs producing acetoacetyl-CoA via a thiolase. Another acetyl-CoA is then condensed making HMG-CoA via HMG-CoA synthase. HMG-CoA undergoes a double reduction by the cofactor NadPH with the enzyme HMG-CoA reductase producing mevalonate. An embodiment can also employ a engineered lepidoptera HMGR that accepts NADH instead of NADPH (such HMGRs are found in nature, though not from lepidotera) in a pathway to make homoterpenes. A phosphate moiety is then added by MevK making MevP. MevP has another phosphate added by the enzyme MevPK making MevPP (at the expense of ATP). MevPP undergoes a decarboxylation catalyzed by the enzyme MevPP decarboxylase, at the expense of an ATP, producing IPP. IPP can be isomerized by IPP isomerase making DMAPP. The prenyltransferase FPP synthase then condenses one IPP and one DMAPP to make GPP. The same enzyme then takes GPP and IPP to produce FPP. FPP is an essential metabolite used to make a large number of compounds including quinones, cell wall components, and sesquiterpenes secondary metabolites among others. FIG. 1.

Lepidoptera Mevalonate Pathway:

Lepidoptera synthesize Juvenile Hormones through the mevalonate pathway as a signaling molecule to regulate body plan and development. While the Lepidoptera mevalonate pathway can catalyze the canonical reactions as mentioned above, it has a relaxed substrate specificity, allowing it to condense propionyl-CoA and acetyl-CoA at the first step of the pathway. Eventually this makes the six carbon building block HIPP, which can then be incorporated into the FPP analogues which become Juvenile Hormones. However, these same FPP analogues, if exposed to a suitable terpene cyclase can cyclize and become novel terpenes. FIG. 2.

Figure 4:
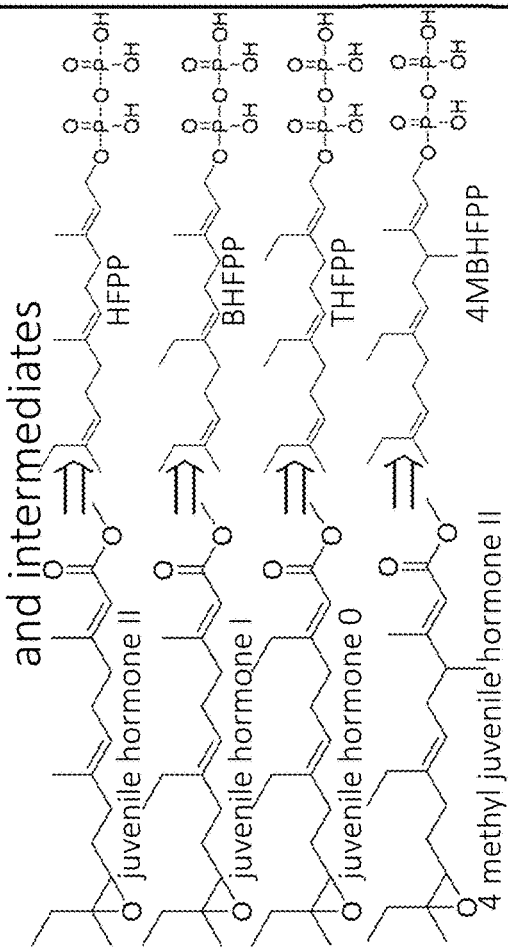

By heterologous expressing the mevalonate pathway enzymes (up to and including FPP synthases) from Lepidoptera species (or functionally equivalent enzymes of other species, particularly insects), coupled with a terpene cyclase, we have been able to make sixteen carbon terpenes. Because of the diversity of JHs available from nature, we can produce compounds containing seventeen and eighteen carbons as well. FIG. 4 shows FPP variants which occur in nature. Our system can also produce the precursor for making eleven and twelve carbon compounds, and by engineering a prenyltransferase(s), C21-24 compounds, C30-35 compounds and so on and so forth can also be created. The invention can be used to make already known terpenes with an ethyl substitution of a methyl group, as well as entirely new backbone configurations as the extra carbons allow novel ways for them to cyclize. These novel compounds have value in the areas where terpenes have traditionally found uses (pharmaceuticals, flavors, fragrances, commodity chemicals and fuels), and because of the modularity of the system, this invention greatly expands the reachable chemical space.

EXAMPLES

In these examples we demonstrate expression constructs of Lepidoptera mevalonate pathway and cyclase for expression in E. coli.

We selected the mevalonate pathway enzymes from Bombyx mori (silkworm) as predicted by Kinjoh T. et al, except for isopentenyl pyrophosphate isomerase (IPPI) and farnesyl pyrophosphate synthase (FPPS) which we sourced from Choristoneura fumiferana (eastern spruce budworm) since they have been studied previously. Soluble expression of HMGR required an N-terminal truncation to remove a membrane associated domain—a similar truncation was required for S. cerevisiae HMGR soluble expression. We could not get the putative thiolase predicted by Kinjoh T. et al, to express in E. coli, so we used another well-characterized thiolase, PhaA from Acinetobacter sp. (strain RA3849).

We constructed a pathway using two plasmids. The upper portion of the pathway, up to HMGR was expressed from a LacUV5 promoter, while the lower half up to IPPI was expressed from the Trc promoter on a plasmid containing the medium copy number p15a origin of replication. We named this construct pJH10 (FIG. 6). The FPP synthases and the well-studied epi-isozizaene synthase from Streptomyces coelicolor A3(2) were placed on a second plasmids under the control of pTrc promoter with the high copy number colE1 origin. We named this construct pJH15.

Figure 3:
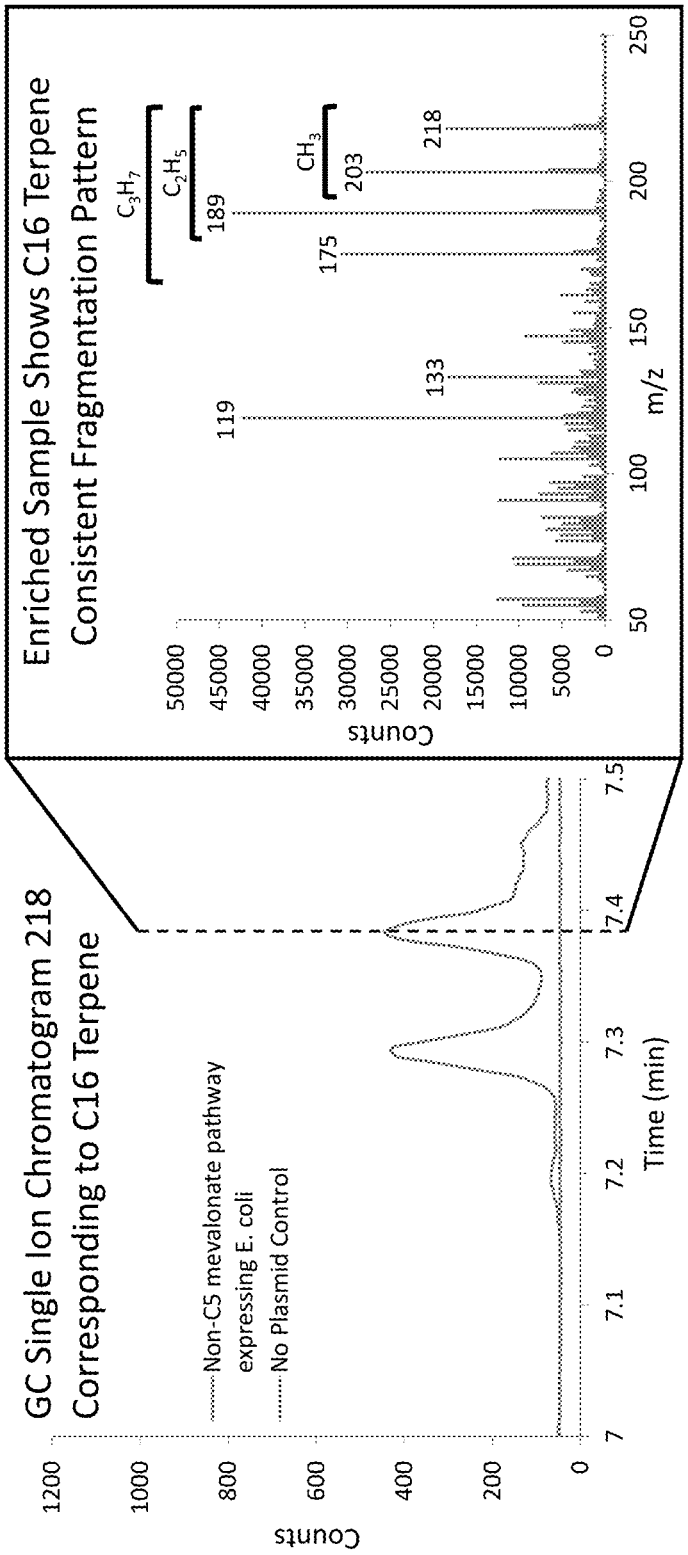

As the expression strain we used the E. coli Bap1 cell line, a BL21DE3* derivative, which contains an inducible propionate CoA ligase. We transformed the cells and grew them in terrific broth supplemented with 0.4% glucose and 1 g/L sodium propionate with a nonane overlay to extract any produced terpenes. We showed that with the addition of the plasmids and propionate, we could see new 218 m/z peaks on GCMS corresponding to a C16 terpenes (FIG. 3). These peaks were contingent on propionate presence in the media. New profiles could be produced by using different cyclases and different mutants of epi-isozizaene synthase.

Since the production of these new peaks was only detectable looking for the 218 m/z ion, we enriched our samples with a rotory evaporator and then used a scanning method to detect the fragmentation. Using this method, we were able to determine that the fragmentation pattern was also consistent with C16 terpenes. The 203 m/z fragment corresponds to a C16 terpene with a methyl group removed. Similarly, the 189 m/z peak corresponds with an ethyl group removed and the 175 m/z peak to a propyl group removed. (FIG. 3).

Because the cell has high flux through acetyl-CoA, and the pathway can accept either acetoacetyl-CoA or 3-ketovaleryl-CoA, we have had difficulties directing flux to make C6 derived terpenes over C5 terpenes. To counter this, we leveraged fatty acid beta oxidation to make 3-ketovaleryl-CoA from exogenously added sodium valerate. We used the Keio collection JW2218 (which lacks the thiolase AtoB) and replaced PhaA from the pJH10 construct with a valeryl-CoA synthase from S. sativa and named the construct pJH53. In addition, we added FadB from E. coli and Aco from Micrococcus luteus behind a pLacUV5 promoter on the pJH15 construct and named the new construct pJH55 (FIG. 7). Via this method, we are able to greatly reduce the amount of C15 terpenes produced, while maintaining the production of C16 terpenes. Alternatively, we could use an enzyme which condenses propionyl-CoA and malonyl-CoA through a decarboxylative Claisen condensation to make 3-ketovaleryl-CoA.

Figure 5:
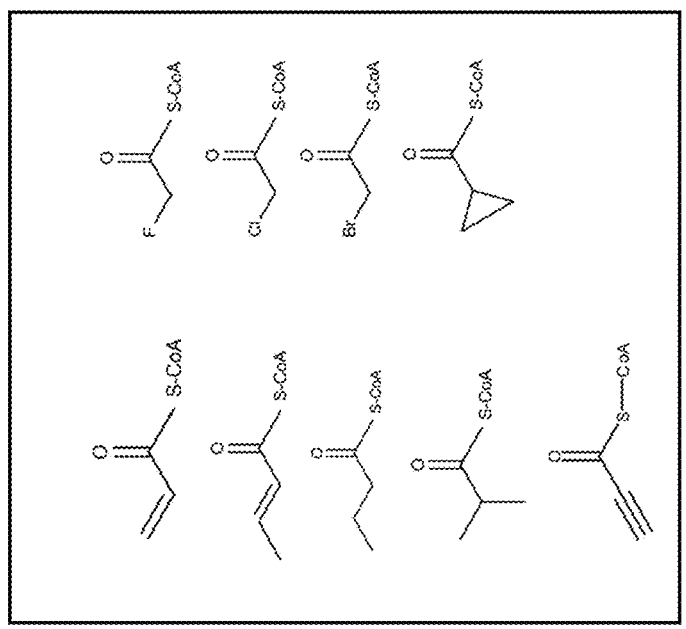

Our initial proof-of-principle demonstrated that the pathway will accept propionyl-CoA, but it can accept larger substrates as well including but not limited to acrylyl-CoA, butyryl-CoA, crotonyl-CoA, isobutyryl-CoA, cyclopropanecarboxyl-CoA, fluoroacetyl-CoA, chloroacetyl-CoA, bromoacetyl-CoA, propioyl-CoA. These alternatives further increase the reachable chemical space, especially if we can add functional groups, which greatly enable semi-synthesis efforts. (FIG. 5).

Figure 8:
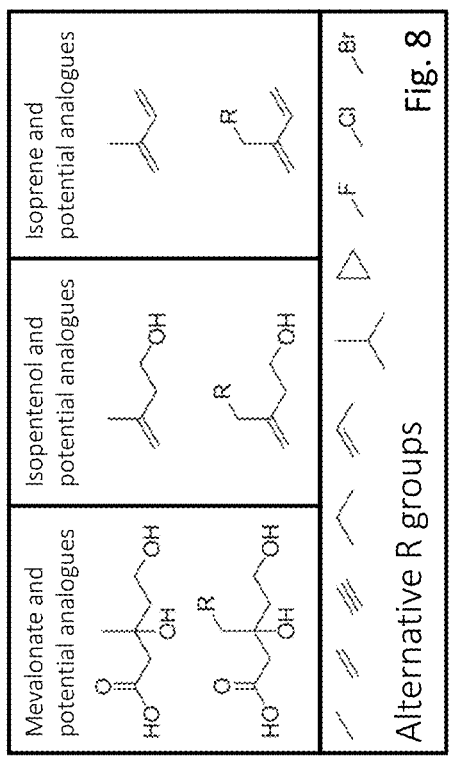

As an example, we have made homomevalonate (FIG. 2, FIG. 8) as an intermediate on the way to C16 terpenes, but it itself can be used as a polymer or a co-polymer. Another alternative embodiment is homoisopentanol which can be used as a fuel or commodity chemical depending on pathways promiscuity, and homoisoprene and derivatives may find uses as polymers. (FIG. 8).

The invention claimed is:

1. A cell genetically engineered to express a heterologous metabolic pathway comprising heterologous *Bombyx mori* and/or *Choristoneura fumiferana* mevalonate pathway enzymes, wherein the cell produces a product of the metabolic pathway that is a C16 terpene, wherein the mevalonate pathway enzymes comprise β-hydroxy β-methylglutaryl-CoA synthase (HMGS), β-hydroxy β-methylglutaryl-CoA reductase (HMGR), mevalonate kinase (MevK), mevalonate phosphate kinase (MevPK), mevalonate pyrophosphate decarboxylase (MevPPD), isopentenyl pyrophosphate isomerase (IPPI) and farnesyl pyrophosphate synthase (FPPS), wherein the metabolic pathway further comprises a terpene cyclase.

2. The cell of claim 1, wherein the terpene cyclase is *Streptomyces coelicolor* epi-isozizaene synthase.

3. The cell of claim 1, wherein the metabolic pathway further comprises propionate-CoA ligase.

4. The cell of claim 1, wherein the metabolic pathway further comprises *S. sativa* valeryl-CoA synthase, *E. coli* FadB and/or *Micrococcus luteus* Aco.

5. The cell of claim 1 that is *E. coli*.

6. A method for producing a C16 terpene product, wherein said method comprises growing the cell of claim 1 to produce the product, and isolating or enriching the product.

7. A method of making the cell of claim 1, wherein said method comprises genetically engineering a cell to comprise a heterologous metabolic pathway comprising a terpene cyclase and heterologous *Bombyx mori* and/or *Choristoneura fumiferana* mevalonate pathway enzymes, wherein the mevalonate pathway enzymes comprise β-hydroxy β-methylglutaryl-CoA synthase (HMGS), β-hydroxy β-methylglutaryl-CoA reductase (HMGR), mevalonate kinase (MevK), mevalonate phosphate kinase (MevPK), mevalonate pyrophosphate decarboxylase (MevPPD), isopentenyl pyrophosphate isomerase (IPPI) and farnesyl pyrophosphate synthase (FPPS), and wherein the cell produces a product of the metabolic pathway that is a C16 terpene.

* * * * *